(12) United States Patent
Ju et al.

(10) Patent No.: US 10,782,275 B2
(45) Date of Patent: Sep. 22, 2020

(54) SEMICONDUCTOR HYDROGEN SENSOR AND MANUFACTURING METHOD THEREOF

(71) Applicant: Boe Technology Group Co., Ltd., Beijing (CN)

(72) Inventors: Changcheng Ju, Beijing (CN); Xiyuan Wang, Beijing (CN); Zhuo Chen, Beijing (CN); Long Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 301 days.

(21) Appl. No.: 15/736,750

(22) PCT Filed: Apr. 27, 2017

(86) PCT No.: PCT/CN2017/082191
§ 371 (c)(1),
(2) Date: Dec. 14, 2017

(87) PCT Pub. No.: WO2018/000926
PCT Pub. Date: Jan. 4, 2018

(65) Prior Publication Data
US 2018/0356380 A1    Dec. 13, 2018

(30) Foreign Application Priority Data
Jun. 27, 2016  (CN) .......................... 2016 1 0483672

(51) Int. Cl.
*G01N 33/00* (2006.01)
*G01N 27/12* (2006.01)
*G01N 27/00* (2006.01)

(52) U.S. Cl.
CPC .......... *G01N 33/005* (2013.01); *G01N 27/00* (2013.01); *G01N 27/12* (2013.01)

(58) Field of Classification Search
CPC ....... G01N 33/005; G01N 27/00; G01N 27/12
See application file for complete search history.

(56) References Cited

U.S. PATENT DOCUMENTS

| 4,347,732 A * | 9/1982 | Leary ................. G01N 33/0014 338/34 |
| 2002/0118027 A1* | 8/2002 | Routkevitch ........... A61L 27/06 324/694 |

(Continued)

FOREIGN PATENT DOCUMENTS

| CN | 101458221 A | 6/2009 |
| CN | 101975803 A | 2/2011 |

(Continued)

OTHER PUBLICATIONS

Zhang, Zhongyang, et al. "Highly enhanced sensitivity of hydrogen sensors using novel palladium-decorated graphene nanoribbon film/ SiO 2/Si structures." Journal of Materials Chemistry A 2.38 (2014): 15931-15937.*

(Continued)

*Primary Examiner* — Robert J Eom
(74) *Attorney, Agent, or Firm* — Womble Bond Dickinson (US) LLP

(57) ABSTRACT

The present disclosure provides a semiconductor hydrogen sensor and a manufacturing method thereof. The semiconductor hydrogen sensor comprises: a substrate; a gas-sensitive material pattern and a metal electrode pattern arranged in a same layer and distributed alternatingly on a side of the substrate; and a two-dimensional material filter layer arranged on a side surface of the gas-sensitive material pattern and the metal electrode pattern facing away from the substrate.

16 Claims, 4 Drawing Sheets

(56) References Cited

U.S. PATENT DOCUMENTS

2015/0273403 A1* 10/2015 Yu ..................... B01D 67/0046
                                                          96/11
2015/0362470 A1   12/2015 Jung et al.

FOREIGN PATENT DOCUMENTS

| CN | 102636522 A | 8/2012 |
| --- | --- | --- |
| CN | 102661978 A | 9/2012 |
| CN | 103063706 A | 4/2013 |
| CN | 103515039 A | 1/2014 |
| CN | 103645216 A | 3/2014 |
| CN | 104034758 A | 9/2014 |
| CN | 104569052 A | 4/2015 |
| CN | 105092654 A | 11/2015 |
| CN | 106198631 A | 12/2016 |

OTHER PUBLICATIONS

Tien, L. C., et al. "Detection of hydrogen with SnO2-coated ZnO nanorods." Applied surface science 253.10 (2007): 4748-4752.*
Office Action received for Chinese Patent Application No. 201610483672.1, dated Feb. 24, 2018, 17 pages (9 pages of English Translation and 8 pages of Office Action).
Written Opinion received for PCT Patent Application No. PCT/CN2017/082191, dated Jun. 12, 2017, 6 pages (2 pages of English Translation and 4 pages of Original Document).
Office Action received for Chinese Patent Application No. 201610483672.1, dated Sep. 12, 2018, 17 pages (10 pages of English Translation and 7 pages of Office Action).
Office Action received for Chinese Patent Application No. 201610483672.1, dated Aug. 28, 2017, 15 pages (8 pages of English Translation and 7 pages of Office Action).
Li et al., "Ultrathin, Molecular-Sieving Graphene Oxide Membranes for Selective Hydrogen Separation", Science, vol. 342, 2013, pp. 95-98.
International Search Report received for PCT Patent Application No. PCT/CN2017/082191, dated Jun. 12, 2017, 8 pages (3 pages of English Translation and 5 pages of Original Document).
Hua et al., "Research Progress in Chemical Reduction of Oxidized Graphene", Materials Review A: Review, vol. 26, No. 12, 2012, 4 pages.
Fengqiang et al., "Application of Graphene in Gas Sensors," Journal of South China Normal University, vol. 45, No. 6, 2013, 7 pages.
Changyuan et al., The Development of Hydrogen Sensors and Related Sensitive Materials, Materials Review, vol. 19, No. 2, Feb. 2005, 4 pages.

* cited by examiner

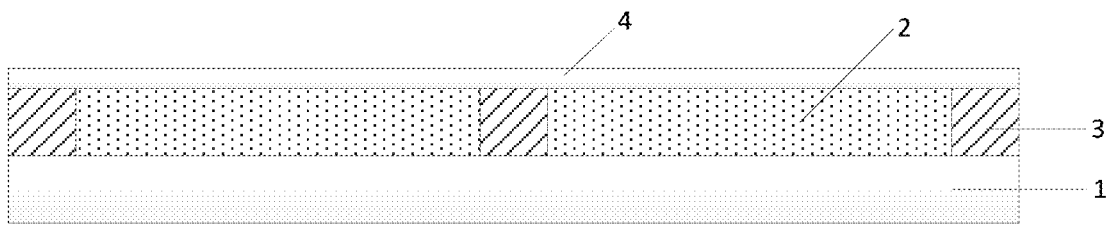
Fig. 1
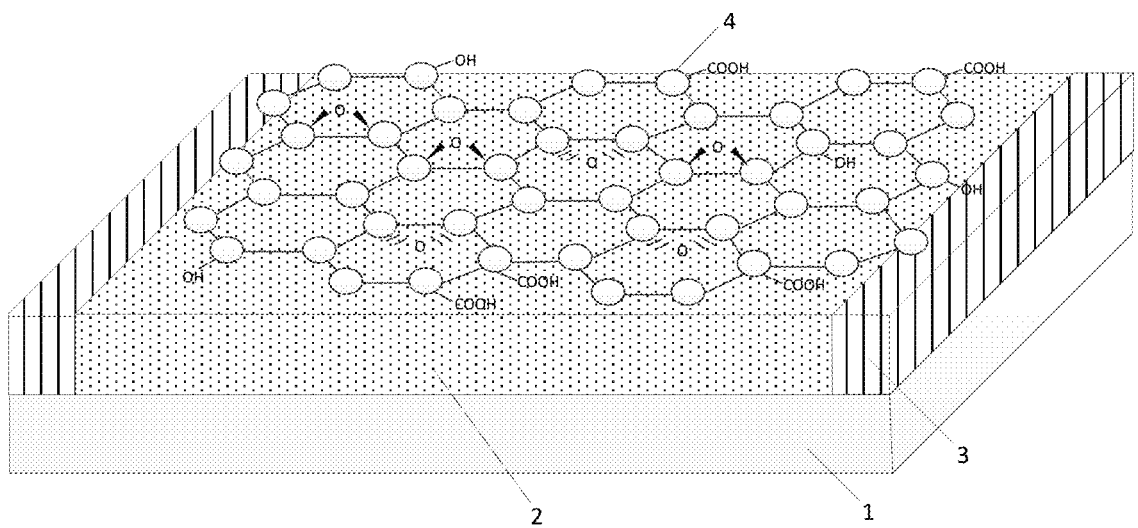
Fig. 2
| forming a gas-sensitive material pattern and a metal electrode pattern arranged in a same layer and distributed alternatingly on a side of the substrate | S1 |
↓
| forming a two-dimensional material filter layer on a side of the gas-sensitive material pattern and the metal electrode pattern facing away from the substrate | S2 |
Fig. 3

SEMICONDUCTOR HYDROGEN SENSOR AND MANUFACTURING METHOD THEREOF

RELATED APPLICATIONS

The present application is the U.S. national phase entry of PCT/CN2017/082191, with an international filling date of Apr. 27, 2017, which claims the benefit of priority from the Chinese patent application No. 201610483672.1 filed on Jun. 27, 2016, the disclosures of which are incorporated herein by reference.

FIELD

The present disclosure relates to the field of sensor technologies, in particular to a semiconductor hydrogen sensor and a manufacturing method thereof.

BACKGROUND ART

Semiconductor gas sensors are the most practical gas sensors which have the widest application range and enjoy the highest popularity among gas detection devices. The semiconductor gas sensors mainly comprise two types: a resistance-type and a non-resistance type. In a resistance-type gas sensor, an electron transfer easily occurs between a sensitive material and a gas, which causes a valent state of the material to change. Finally, different gases and concentrations thereof can be identified based on different resistances of the semiconductor. Such a sensor has many advantages such as high sensitivity, operation convenience, small volume, low cost, short response time, and short recovery time. However, metal oxides are generally responsive to reducing gases, i.e., they are not uniquely responsive to hydrogen. Therefore, a semiconductor hydrogen sensor usually has a poor selectivity. A. Katsuki and K. Fukui et al proposed to modify a surface of a gas-sensitive material and deposit a dense layer in a form of molecular sieves on a tin dioxide surface by chemical vapor deposition. The dense layer prevents diffusion of gases other than hydrogen. Disadvantageously, due to the molecular sieves characteristics of the dense layer, oxygen cannot be diffused into the tin dioxide layer. In this case, after tin dioxide is gradually reduced by hydrogen, output signals of the sensor will rapidly attenuate. As a result, the sensitivity for hydrogen is significantly decreased. Thus, a service life of the sensor is shortened, and the sensing cost is increased, and so on. In view of this, how to manufacture a semiconductor gas sensor that have high permeability for hydrogen molecules, long service life and high sensitivity, etc., is a long pursuit of a developer. A semiconductor gas sensor with these excellent performances improves the test accuracy, enlarge the application range and reduce the device cost. This helps to provide a favorable congenital condition for a market expansion of the product.

At present, a nanocomposite containing graphene and tin dioxide can be used as a gas-sensitive thin film. In this case, the graphene part will also be included in the measurement of resistance. Such gas-sensitive materials can improve performances of the sensor to some degree, but they still have defects such as poor selectivity and low accuracy.

SUMMARY

In one aspect, the present disclosure provides a semiconductor hydrogen sensor, comprising: a substrate; a gas-sensitive material pattern and a metal electrode pattern arranged in a same layer and distributed alternatingly on a side of the substrate; and a two-dimensional material filter layer arranged on a side of the gas-sensitive material pattern and the metal electrode pattern facing away from the substrate.

Optionally, as compared with other reducing gases, the two-dimensional material filter layer has a higher permeability for hydrogen.

Optionally, the two-dimensional material filter layer has a monolayer or multilayer structure.

Optionally, the two-dimensional material filter layer is an oxidized two-dimensional material filter layer.

Optionally, the two-dimensional material filter layer is made of a material selected from a group containing graphene oxides, silylene oxides, phosphorene oxides, stanene oxides, and transition metal sulfides.

Optionally, the gas-sensitive material pattern is made of a material selected from a group containing tin oxides ($SnO_2$), tungsten trioxides ($WO_3$), molybdenum trioxides ($MoO_3$), composite semiconductor materials comprising perovskite ($ABO_3$) and $K_2NiF_4$ ($A_2BO_4$), phthalocyanine, porphyrin, porphine, and tin oxides ($SnO_2$) doped with noble metals.

Optionally, the gas-sensitive material pattern is a gas-sensitive material thin film pattern. Alternatively, the gas-sensitive material pattern comprises one of gas-sensitive material nanowires and gas-sensitive material nanoparticles.

Optionally, the metal electrode pattern is made of a material selected from a group containing Pd, Cu, and an alloy of Al/Mo.

Optionally, the semiconductor hydrogen sensor further comprises an insulating layer. The insulating layer is arranged between the metal electrode pattern and the two-dimensional material filter layer and patterned to correspond to the metal electrode pattern.

Optionally, the semiconductor hydrogen sensor further comprises: an encapsulation layer arranged on a side of the two-dimensional material filter layer facing away from the metal electrode pattern. The encapsulation layer is patterned to correspond to the metal electrode pattern.

In another aspect, the present disclosure provides a method for manufacturing a semiconductor hydrogen sensor. The method comprises: forming a gas-sensitive material pattern and a metal electrode pattern in a same layer on a side of the substrate, the gas-sensitive material pattern and the metal electrode pattern being distributed alternatingly; and forming a two-dimensional material filter layer on a side of the gas-sensitive material pattern and the metal electrode pattern facing away from the substrate.

Optionally, as compared with other reducing gases, the two-dimensional material filter layer has a higher permeability for hydrogen.

Optionally, the two-dimensional material filter layer is formed as a monolayer or multilayer structure.

Optionally, the two-dimensional material filter layer is an oxidized two-dimensional material filter layer.

Optionally, the step of forming a gas-sensitive material pattern and a metal electrode pattern in a same layer on a side of the substrate comprises: depositing a gas-sensitive material thin film layer on a side of the substrate; etching the gas-sensitive material thin film layer to form a plurality of grooves arranged at intervals, the grooves penetrating the gas-sensitive material thin film layer; and depositing a metal electrode material into the plurality of grooves by a magnetron sputtering process, so as to form a gas-sensitive material pattern and a metal electrode pattern distributed alternatingly.

Optionally, the method described above further comprises a step of: after forming a gas-sensitive material pattern and a metal electrode pattern in a same layer on a side of the substrate, forming an insulating layer on the metal electrode pattern, the insulating layer being patterned to correspond to the metal electrode pattern.

Optionally, the method described above further comprises a step of: forming an encapsulation layer on a side of the two-dimensional material filter layer facing away from the metal electrode pattern, the encapsulation layer being patterned to correspond to the metal electrode pattern.

Optionally, the step of forming an encapsulation layer comprises: forming a thin film encapsulation layer on a side of the two-dimensional material filter layer facing away from the metal electrode pattern by a thermal evaporation process; and etching the thin film encapsulation layer with a fine metal mask to form a patterned encapsulation layer.

BRIEF DESCRIPTION OF THE DRAWINGS

In order to illustrate technical solutions of the present disclosure more clearly, drawings to be used will be briefly introduced below. Apparently, the drawings in the following depictions are only some embodiments of the present disclosure. For those having ordinary skills in the art, other drawings can be further obtained from these drawings without any inventive efforts.

FIG. 1 is a partial schematic section view of a semiconductor hydrogen sensor according to one embodiment of the present disclosure;

FIG. 2 is a schematic side view of a semiconductor hydrogen sensor according to another embodiment of the present disclosure;

FIG. 3 is a schematic flow diagram of a method for manufacturing a semiconductor hydrogen sensor according to an embodiment of the present disclosure;

DETAILED DESCRIPTION OF THE EMBODIMENTS

Figure 4:
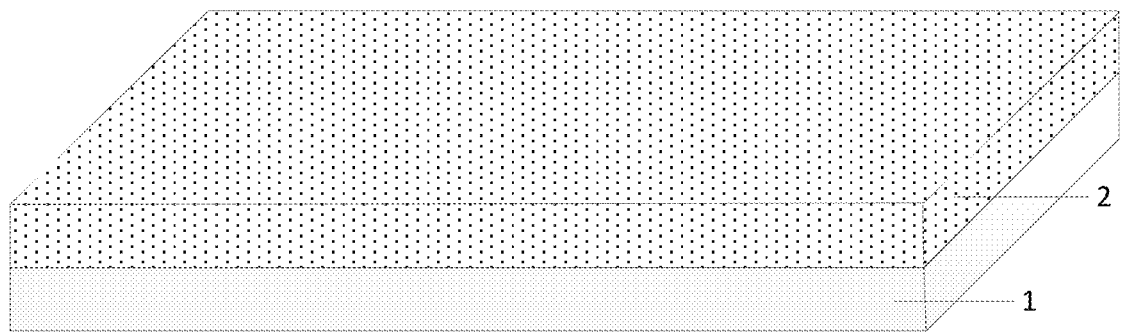
FIG. 4 is a schematic view of a gas-sensitive material thin film layer formed in the method for manufacturing a semiconductor hydrogen sensor according to an embodiment of the present disclosure.

Technical solutions in the present disclosure will be described below clearly and completely with reference to the drawings. Apparently, the described embodiments are only part of embodiments of the present disclosure, instead of all of them. Based on the embodiments of the present disclosure, all other embodiments, obtainable by those having ordinary skills in the art without inventive efforts, shall fall within the protection scope of the present disclosure.

In FIGS. 1-2 and 4-9, 1 represents a substrate; 2 represents a gas-sensitive material pattern; 3 represents a metal electrode pattern; 4 represents a two-dimensional material filter layer; 5 represents an insulating layer; and 6 represents an encapsulation layer.

FIG. 1 is a partial schematic section view of a semiconductor hydrogen sensor according to one embodiment of the present disclosure. FIG. 2 is a schematic side view of a semiconductor hydrogen sensor according to another embodiment of the present disclosure. As shown in FIGS. 1 and 2, the semiconductor hydrogen sensor proposed by the present disclosure comprises: a substrate 1; a gas-sensitive material pattern 2 and a metal electrode pattern 3 arranged in a same layer and distributed alternatingly on a side of the substrate 1; and a two-dimensional material filter layer 4 arranged on a side of the gas-sensitive material pattern 2 and the metal electrode pattern 3 facing away from the substrate 1. In FIG. 1, the two-dimensional material filter layer 4 with a monolayer structure is shown schematically in FIG. 1. Apparently, as is obvious for one skilled in the art, such a two-dimensional material filter layer 4 can also have a multilayer structure, and the present disclosure will not be limited thereto.

As can be seen, in the present embodiment, a two-dimensional material is used as a filter layer for the gas-sensitive material pattern 2 in the semiconductor hydrogen sensor. As shown in FIG. 2, the two-dimensional material has a dense hexagonal structure. This means that the two-dimensional material filter layer 4 prevents most macromolecules from passing through. For common reducing gases, only hydrogen molecules have high permeability. For example, when reducing gases such as $H_2$, CO and NO, as well as macromolecules such as vapor encounter a two-dimensional molecular material layer 4, only hydrogen molecules successfully pass through it and arrive at the gas-sensitive material pattern 2, thereby leading to a reduction reaction. As a result, the gas-sensitive material pattern 2 can only react with hydrogen passing through the two-dimensional material filter layer 4. In this way, the two-dimensional material filter layer 4 is extremely selective. Thus, the semiconductor hydrogen sensor obtains an improved selectivity and sensitivity.

In an optional embodiment of the present disclosure, as shown in FIG. 2, the two-dimensional material filter layer 4 is an oxidized two-dimensional material filter layer.

In this embodiment, as shown in FIG. 2, an oxidized two-dimensional material is used as a filter layer for the gas-sensitive material pattern 2 in the semiconductor hydrogen sensor. The oxidized two-dimensional material comprises materials such as graphene oxides. Graphene oxides have a dense hexagonal structure and prevent most macromolecules from passing through. However, for common reducing gases, only hydrogen molecules have a high permeability such that the gas-sensitive material can only react with hydrogen. In this way, the semiconductor hydrogen sensor has a very high selectivity and sensitivity. Meanwhile, as shown in FIG. 2, the oxidized two-dimensional material is further rich in oxygen-containing functional groups. The oxygen-containing functional groups can re-oxidize the gas-sensitive material in the gas-sensitive material pattern which has been reduced previously, and thus recover its gas-sensitive functionality. This helps to greatly prolong a service life of the semiconductor hydrogen sensor and improve the accuracy.

For example, the two-dimensional material filter layer 4 in the above embodiment can be made of a material selected from a group containing oxidized two-dimensional materials such as graphene oxides, silylene oxides, phosphorene oxides, stanene oxides, and transition metal sulfides.

For example, the gas-sensitive material pattern 2 in the above embodiment can be made of a material selected from a group containing tin oxides $SnO_2$, tungsten trioxides $WO_3$, molybdenum trioxides $MoO_3$, composite semiconductor materials comprising perovskite $ABO_3$ and $K_2NiF_4$ ($A_2BO_4$), polymer materials such as phthalocyanine, porphyrin, porphine and derivatives thereof (of phthalocyanine, porphyrin, porphine), as well as tin oxides $SnO_2$ doped with noble metals (such as Ru, Pd, or Ag).

For example, the gas-sensitive material pattern 2 can be a gas-sensitive material thin film pattern. The gas-sensitive material pattern 2 can further comprise gas-sensitive material nanowires or gas-sensitive material nanoparticles, which will not be limited in this embodiment.

For example, the metal electrode pattern 3 can be made of materials such as Pd, Cu or an alloy of Al/Mo.

Specifically, the metal electrode pattern 3 is used for inputting a measurement voltage and measuring changes in an output current. Thus, the above mentioned electrically conductive metal materials are adopted.

Figure 8:
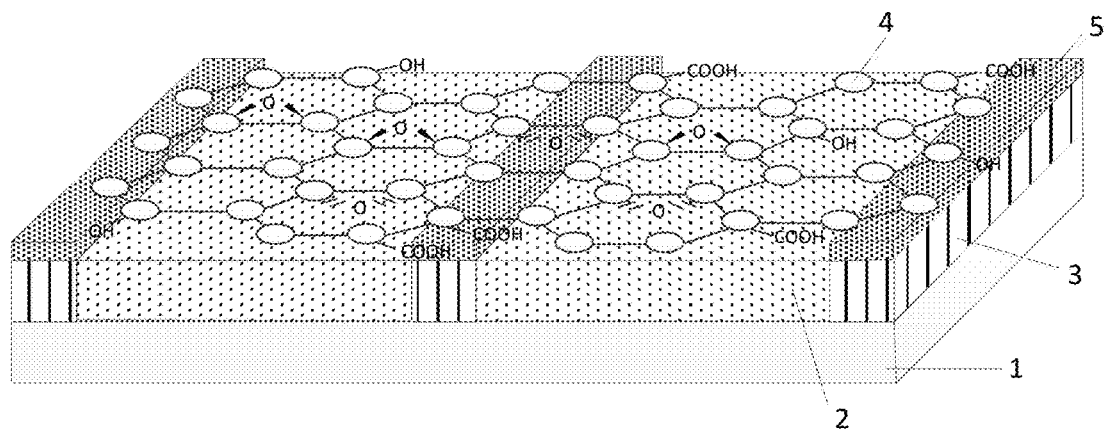
FIG. 8 is a schematic view of a two-dimensional material filter layer formed in the method for manufacturing a semiconductor hydrogen sensor according to an embodiment of the present disclosure.

In an optional embodiment of the present disclosure, in addition to the substrate 1, the gas-sensitive material pattern 2, the metal electrode pattern 3 and the two-dimensional material filter layer 4 in the above embodiment, the semiconductor hydrogen sensor further comprises: an insulating layer 5 formed between the metal electrode pattern 3 and the two-dimensional material filter layer 4, as shown in FIG. 8.

It should be noted that the insulating layer 5 and the metal electrode pattern 3 in the present embodiment are patterned correspondingly. In other words, the insulating layer 5 has a same shape as the metal electrode pattern 3. The insulating layer 5 is arranged between the metal electrode pattern 3 and the two-dimensional material filter layer 4. Since the two-dimensional material filter layer 4 is electrically conductive to some degree, an insulating layer 5 is required to separate the metal electrode pattern 3 from the two-dimensional material filter layer 4.

Furthermore, in an optional embodiment of the present disclosure, in addition to the substrate 1, the gas-sensitive material pattern 2, the metal electrode pattern 3 and the two-dimensional material filter layer 4 in the above embodiment, the semiconductor hydrogen sensor further comprises: an encapsulation layer formed on a side of the two-dimensional material filter layer facing away from the metal electrode pattern. Specifically, the encapsulation layer and the metal electrode pattern are patterned correspondingly. In other words, the encapsulation layer has a same shape as the metal electrode pattern.

Figure 9:
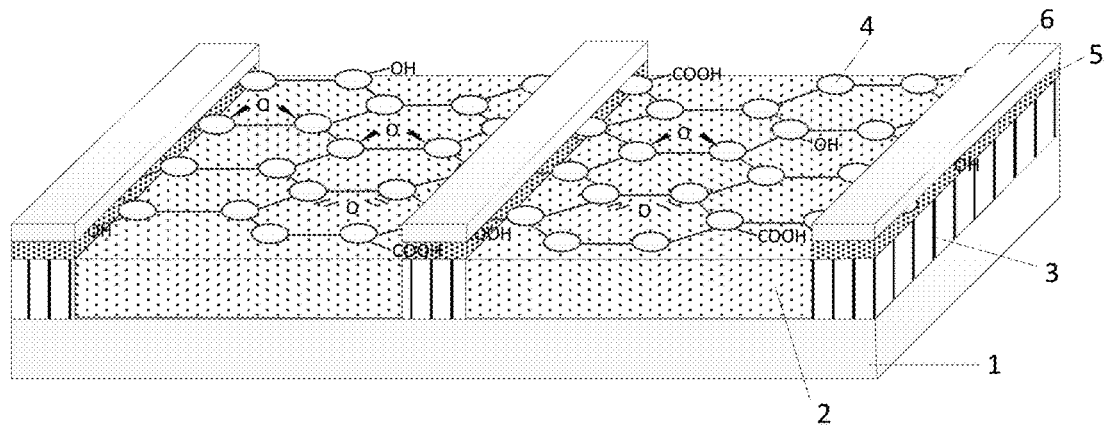
FIG. 9 is a schematic view of an encapsulation layer formed in the method for manufacturing a semiconductor hydrogen sensor according to an embodiment of the present disclosure.

For example, as shown in FIG. 9, the semiconductor hydrogen sensor comprises: a substrate 1, a gas-sensitive material pattern 2, a metal electrode pattern 3, a two-dimensional material filter layer 4, an insulating layer 5, and an encapsulation layer 6.

In the present embodiment, since the two-dimensional material filter layer 4 is very thin, the encapsulation layer 6 is used to secure the two-dimensional material filter layer 4, in order to prevent the two-dimensional material filter layer 4 from falling off and protect the gas-tightness of edges thereof.

FIG. 3 is a schematic flow diagram of a method for manufacturing a semiconductor hydrogen sensor according to an embodiment of the present disclosure. As shown in FIG. 3, the method comprises steps as follows: S1, forming a gas-sensitive material pattern and a metal electrode pattern arranged in a same layer and distributed alternatingly on a side of the substrate; and S2, forming a two-dimensional material filter layer with a monolayer or multilayer is structure on a side of the gas-sensitive material pattern and the metal electrode pattern facing away from the substrate.

As can be seen, in the present embodiment, a two-dimensional material is used as a filter layer for the gas-sensitive material pattern in the semiconductor hydrogen sensor. Such a two-dimensional material has a dense hexagonal structure and prevents most macromolecules from passing through. However, for common reducing gases, only hydrogen molecules have high permeability. For example, when reducing gases such as $H_2$, CO and NO, as well as macromolecules such as vapor encounter a two-dimensional molecular material layer, only hydrogen molecules can successfully pass through it and arrive at the gas-sensitive material pattern, thereby leading to a reduction reaction. As a result, the gas-sensitive material pattern can only react with hydrogen passing through the two-dimensional material filter layer. In this way, the two-dimensional material filter layer is extremely selective. Thus, the semiconductor hydrogen sensor obtains improved selectivity and sensitivity.

In an optional embodiment of the present disclosure, the two-dimensional material filter layer is an oxidized two-dimensional material filter layer.

In this embodiment, an oxidized two-dimensional material is used as a filter layer for the gas-sensitive material pattern in the semiconductor hydrogen sensor. The oxidized two-dimensional material comprises materials such as graphene oxides. Graphene oxides have a dense hexagonal structure and prevent most macromolecules from passing through. For common reducing gases, only hydrogen molecules have high permeability such that the gas-sensitive material can only react with hydrogen. In this way, the semiconductor hydrogen sensor has a very high selectivity and sensitivity. Meanwhile, the oxidized two-dimensional material is further rich in oxygen-containing functional groups. The oxygen-containing functional groups can re-oxidize the gas-sensitive material in the gas-sensitive material pattern which has been reduced previously, and recover its gas-sensitive functionality. This greatly prolongs a service life of the semiconductor hydrogen sensor and improves the accuracy.

In an optional embodiment of the present disclosure, the step S1 is specifically comprises sub-steps as follows: S11, depositing a gas-sensitive material thin film layer on a side of the substrate; S12, etching the gas-sensitive material thin film layer to form a plurality of grooves arranged at intervals, the grooves penetrating the gas-sensitive material thin film layer; and S13, depositing a metal electrode layer into the plurality of grooves by a magnetron sputtering process, so as to form a gas-sensitive material pattern and a metal electrode pattern distributed alternatingly.

Furthermore, in an optional embodiment of the present disclosure, the method further comprises: forming an insulating layer on the metal electrode pattern, after step S1 and before step S2.

In this embodiment, the insulating layer and the metal electrode pattern are patterned correspondingly. In other words, the insulating layer has a same shape as the metal electrode pattern. As such, the insulating layer is arranged between the metal electrode pattern and the two-dimensional material filter layer. Since the two-dimensional material filter layer is electrically conductive to some degree, an insulating layer is needed to separate the metal electrode pattern from the two-dimensional material filter layer.

Furthermore, in an optional embodiment of the present disclosure, the method further comprises: forming an encapsulation layer on a side of the two-dimensional material filter layer facing away from the metal electrode pattern, after step S2 and before step S3.

In this embodiment, the encapsulation layer and the metal electrode pattern are patterned correspondingly. In other words, the encapsulation layer has a same shape as the metal electrode pattern. Since the two-dimensional material filter layer is very thin, the encapsulation layer is used to secure the two-dimensional material filter layer, in order to prevent the two-dimensional material filter layer from falling off and protect the gas-tightness of edges thereof.

Specifically speaking, the formation of the encapsulation layer in step S3 can be implemented by steps as follows: S31, forming a thin film encapsulation layer on a side of the two-dimensional material filter layer facing away from the metal electrode pattern by a thermal evaporation process; and S32, etching the thin film encapsulation layer with a fine metal mask to form a patterned encapsulation layer.

In order to render technical solutions of the present disclosure clearer, a specific embodiment of the present disclosure will be illustrated below with reference to schematic side views of the device structure formed after each step. In this embodiment, as shown by the final product structure in FIG. 9, the semiconductor hydrogen sensor comprises: a substrate 1, a gas-sensitive material pattern 2, a metal electrode pattern 3, a two-dimensional material filter layer 4, an insulating layer 5, and an encapsulation layer 6. Of course, the semiconductor hydrogen sensor can further comprise other structures, which will not be detailed herein for simplicity. It should be understood that the structure shown here is only exemplary. There can be other structure forms according to the scope and spirit defined in the claims of the present disclosure.

Figure 10:
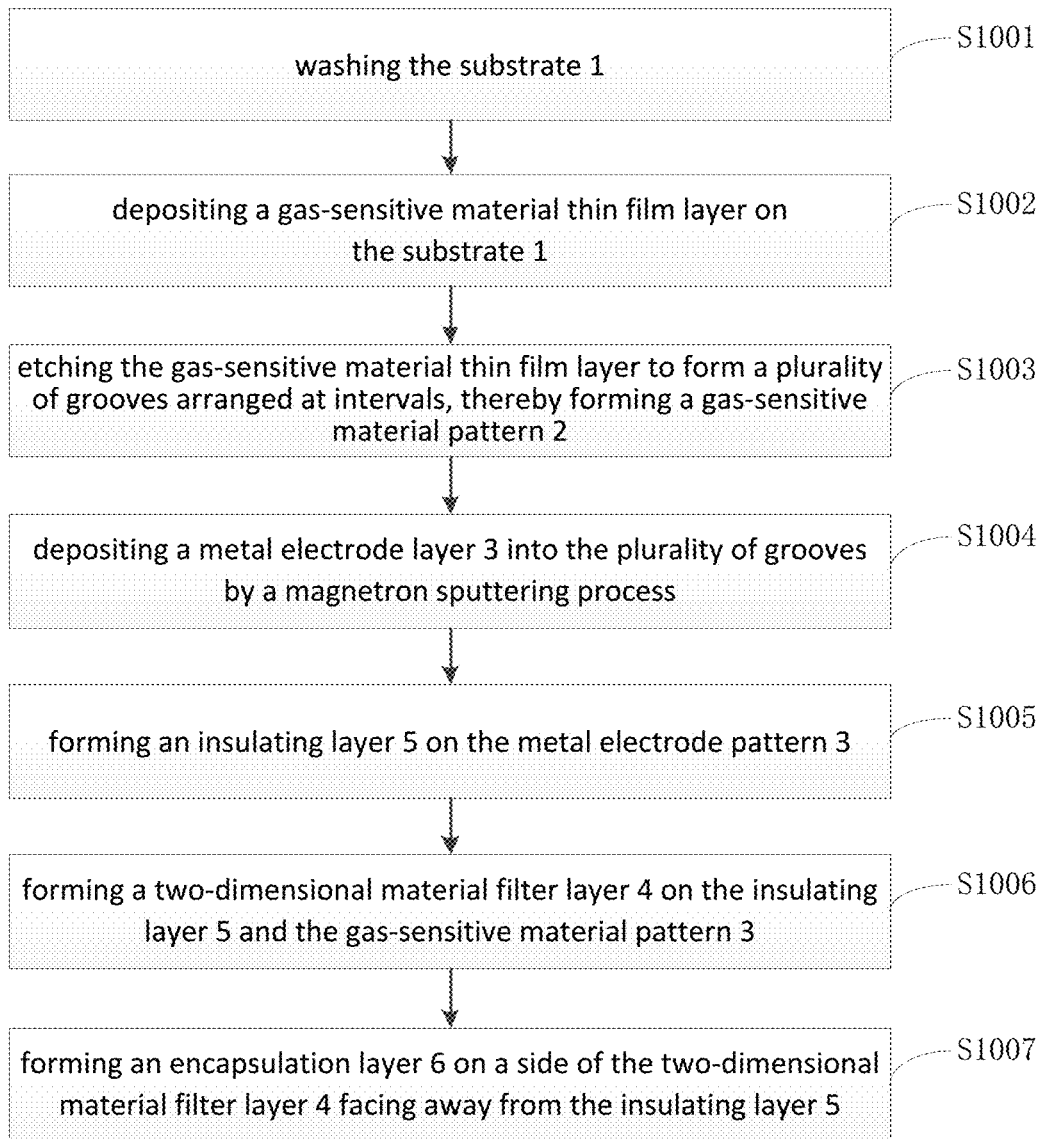
FIG. 10 is a schematic flow diagram of a method for manufacturing a semiconductor hydrogen sensor according to another embodiment of the present disclosure.

As shown in FIG. 10, in this embodiment, the method for manufacturing a semiconductor hydrogen sensor can specifically comprise steps as follows.

S1001: washing the substrate 1.

Specifically, the substrate 1 can be a transparent glass substrate, a Si substrate or the like, which will not be limited in the present disclosure. Specifically, the substrate 1 is washed by an existing standard process, which will not be detailed herein for simplicity.

S1002: depositing a gas-sensitive material thin film layer on the substrate 1, as shown in FIG. 4.

For example, if $SnO_2$ is used as a gas-sensitive material, $SnCl_2$ is prepared as a raw material for Sn, and $O_2$ carried by Ar enters a reaction cavity and serves as an O source. Furthermore, a $SnO_2$ thin film is deposited by plasma enhanced chemical vapor deposition (PECVD for short). In this case, the power source has a frequency of 40.68 MHz, a power of 200 W, and a voltage of 600V. In the meantime, a working gas pressure is 200 Pa, a deposition time is 20 min, and a heating temperature for the substrate is 150° C.

Furthermore, this procedure further comprises an annealing step. For example, the substrate is annealed for 40 min in air, wherein an annealing temperature is 4000° C., and a thickness is 200 nm.

Figure 5:
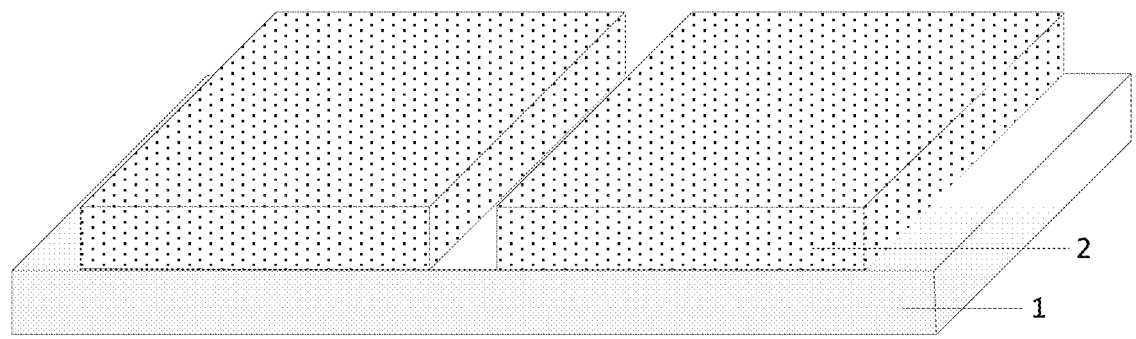
FIG. 5 is a schematic view of a gas-sensitive material pattern formed in the method for manufacturing a semiconductor hydrogen sensor according to an embodiment of the present disclosure.

S1003: etching the gas-sensitive material thin film layer to form a plurality of grooves arranged at intervals, thereby forming a gas-sensitive material pattern 2, as shown in FIG. 5.

For example, an electrode pattern is formed by photolithography, and the gas-sensitive material pattern 2 (such as $SnO_2$) is formed by dry etching. Specifically, the electrode pattern corresponds to the plurality of grooves arranged at intervals on the gas-sensitive thin film layer 2.

Figure 6:
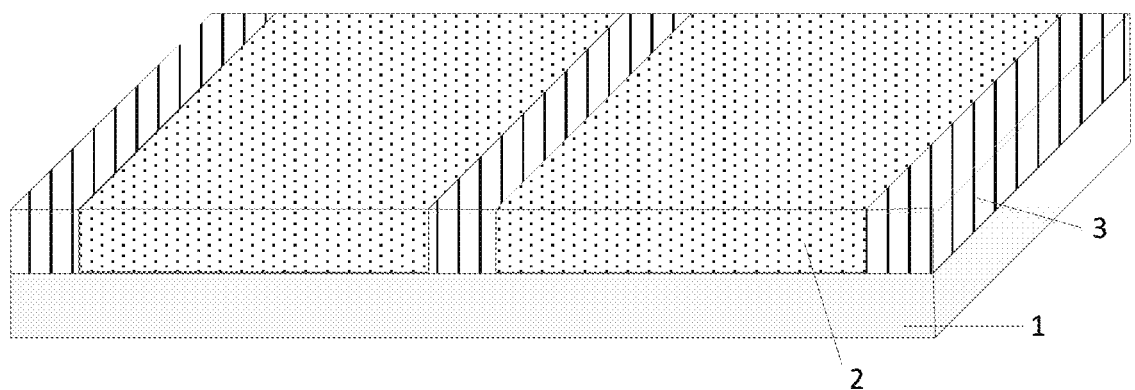
FIG. 6 is a schematic view of a metal electrode pattern formed in the method for manufacturing a semiconductor hydrogen sensor according to an embodiment of the present disclosure.

S1004: depositing a metal electrode layer 3 into the plurality of grooves by a magnetron sputtering process, as shown in FIG. 6.

For example, a metal electrode Mo/Al of 200 nm can be specifically deposited at 150° C. by a magnetron sputtering process, so as to form a metal electrode pattern 3.

Figure 7:
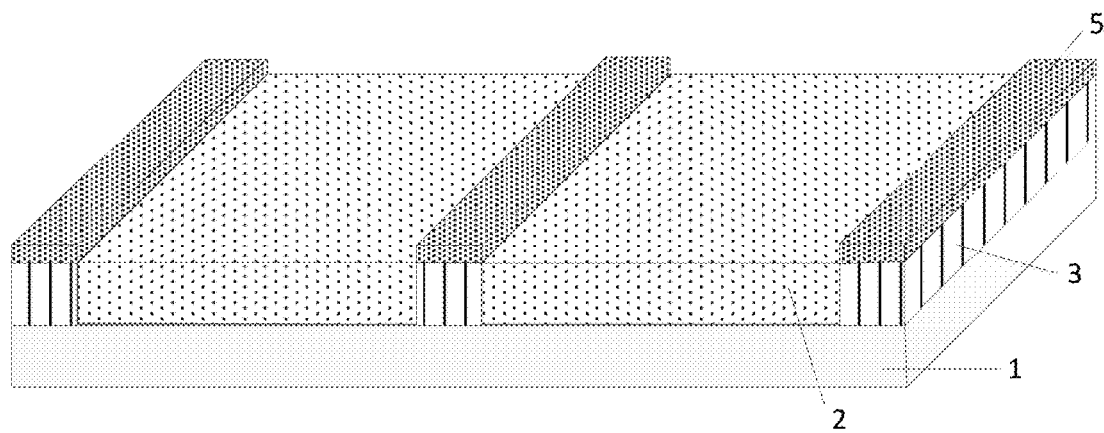
FIG. 7 is a schematic view of an insulating layer formed in the method for manufacturing a semiconductor hydrogen sensor according to an embodiment of the present disclosure.

S1005: forming an insulating layer 5 on the metal electrode pattern 3, as shown in FIG. 7.

Specifically, the insulating layer 5 is arranged to correspond to the metal electrode pattern 3. In particular, the insulating layer 5 has a same shape as the metal electrode pattern 3.

For example, a $SiO_2$ insulating layer is prepared on the metal electrode pattern 3 by chemical vapor deposition (CVD for short) with a thickness of about 100-300 nm.

S1006: forming a two-dimensional material filter layer 4 on the insulating layer 5 and the gas-sensitive material pattern 3, as shown in FIG. 8.

For example, a natural flake graphite can be oxidized by an improved Hummers process and sonicated for 90 min, so as to prepare an oxidized graphene dispersion. After that, the oxidized graphene dispersion is spin-coated onto a tin oxide substrate, then dried and cured at 80° C., thereby forming a graphene oxide as a two-dimensional material filter layer 4.

Specifically, the improved Hummers process comprises a procedure as follows. Concentrated $H_2SO_4$ is cooled to 0° C. and stirred together with graphite, and then $NaNO_3$ and $KMnO_4$ are added sequentially. A first reaction is conducted at 4° C. and lasts for 90 min. A second reaction is conducted at 36° C. and lasts for 30 min. A third reaction is conducted at 85° C. and lasts for 30 min. Furthermore, the mixture is purified by means of a centrifuge until it contains no sulfonic acid groups, and then dried at 45° C., thereby forming graphene oxides.

S1007: forming an encapsulation layer 6 on a side of the two-dimensional material filter layer 4 facing away from the insulating layer 5, as shown in FIG. 9.

Specifically, the encapsulation layer 6 is arranged to correspond to the metal electrode pattern 3 or the insulating layer 5. In particular, the encapsulation layer 6 has a same shape as the metal electrode pattern 3 or the insulating layer 5.

For example, the layer undergoes thin film encapsulation (TFE) by thermal evaporation, and a pattern of encapsulation layer 6 is formed by means of a fine metal mask. After that, the two-dimensional material layer 4 is further secured, and the gas-tightness of the edges thereof is protected. Thereby, a semiconductor hydrogen sensor element structure is formed.

Furthermore, the manufacturing method described above further comprises steps for testing and analyzing the formed semiconductor hydrogen sensor, which will not be detailed herein for simplicity.

It should be noted that in describing the present disclosure, terms indicating directional or positional relationships such as "up" and "down" are used on a basis of the directional or positional relationships shown in the drawings. They are only used for facilitating depiction of the present disclosure, rather than indicating or implying that the indicated device or element must have a particular direction or be constructed or operated in a particular direction. So, they cannot be construed as limiting the present disclosure. Unless explicitly prescribed and defined otherwise, terms such as "mount", "connect" and "link" should be understood in a broad sense. For example, the connection can be fixed connection, detachable connection or integral connection. Alternatively, it can be direct connection, indirect connection via an intermediate medium, or connection inside two elements. For one having ordinary skills in the art, specific meanings of the above terms in the present disclosure can be understood based on specific situations.

It should be further noted that relational terms such as "first" and "second" herein are only used for distinguishing an entity or operation from another entity or operation. They do not necessarily require or imply any such actual relation or sequence between these entities or operations. Moreover, terms such as "include", "comprise" or other variants are intended to be non-exclusive. In other words, a process, a method, an object or a device comprising a series of elements comprise not only those elements, but also other elements not explicitly listed, or elements inherent to the process, the method, the object or the device. Without more limitations, elements defined by the wording "comprise a . . ." does not exclude the presence of further same elements in the process, the method, the object or the device comprising said elements.

The above embodiments are only used for illustrating technical solutions of the present disclosure, instead of limiting them in any sense. Although the present disclosure has been depicted in detail with reference to the above embodiments, one having ordinary skills in the art should understand that the technical solutions stated in each embodiment can be modified, or part of the technical features can be replaced by equivalents. Such modification or replacement does not make the essence of the corresponding technical solutions depart from the spirit and scope of the technical solutions in each embodiment of the present disclosure.

The invention claimed is:

1. A semiconductor hydrogen sensor, comprising:
a substrate;
a gas-sensitive material pattern and a metal electrode pattern arranged in a same layer and distributed alternatingly on a side of the substrate; and
a two-dimensional material filter layer arranged on a side of the gas-sensitive material pattern and the metal electrode pattern facing away from the substrate,
a patterned insulating layer between the metal electrode pattern and the two-dimensional material filter layer, and
a patterned encapsulation layer on a side of the two-dimensional material filter layer facing away the metal electrode pattern,
wherein the two-dimensional material filter layer covers the gas-sensitive material pattern and the metal electrode pattern, each of a pattern of the patterned insulating layer and a pattern of the patterned encapsulation layer is consistent with a pattern of the metal electrode pattern, and orthographic projections of the patterned encapsulation layer and the patterned insulating layer on the substrate substantially overlap an orthographic projection of the metal electrode pattern on the substrate, wherein the two-dimensional material filter layer is made of a material selected from a group containing silylene oxides, phosphorene oxides, stanene oxides and transition metal sulfides.

2. The semiconductor hydrogen sensor according to claim 1, wherein the two-dimensional material filter layer has a higher permeability for hydrogen, as compared with other reducing gases.

3. The semiconductor hydrogen sensor according to claim 1, wherein the two-dimensional material filter layer has a monolayer or multilayer structure.

4. The semiconductor hydrogen sensor according to claim 1, wherein the two-dimensional material filter layer is an oxidized two-dimensional material filter layer.

5. The semiconductor hydrogen sensor according to claim 1, wherein the gas-sensitive material pattern is made of a material selected from a group containing tin oxides ($SnO_2$), tungsten trioxides ($WO_3$), molybdenum trioxides ($MoO_3$), composite semiconductor materials comprising perovskite ($ABO_3$) and $K_2NiF_4$ ($A_2BO_4$), phthalocyanine, porphyrin, porphine, and tin oxides ($SnO_2$) doped with noble metals.

6. The semiconductor hydrogen sensor according to claim 1, wherein the gas-sensitive material pattern comprises one of gas-sensitive material nanowires and gas-sensitive material nanoparticles.

7. The semiconductor hydrogen sensor according to claim 1, wherein the gas-sensitive material pattern comprises a gas-sensitive material thin film pattern.

8. The semiconductor hydrogen sensor according to claim 1, wherein the metal electrode pattern is made of a material selected from a group containing Pd, Cu, and an alloy of Al/Mo.

9. A method for manufacturing the semiconductor hydrogen sensor according to claim 1, comprising:
forming the gas-sensitive material pattern and the metal electrode pattern in a same layer on a side of the substrate, the gas-sensitive material pattern and the metal electrode pattern being distributed alternatingly; and
forming the two-dimensional material filter layer on a side of the gas-sensitive material pattern and the metal electrode pattern facing away from the substrate.

10. The method according to claim 9, wherein the two-dimensional material filter layer has a higher permeability for hydrogen, as compared with other reducing gases.

11. The method according to claim 9, wherein the two-dimensional material filter layer is formed as a monolayer or multilayer structure.

12. The method according to claim 9, wherein the two-dimensional material filter layer is an oxidized two-dimensional material filter layer.

13. The method according to claim 9, wherein the step of forming a gas-sensitive material pattern and a metal electrode pattern in a same layer on a side of the substrate comprises:
depositing a gas-sensitive material thin film layer on a side of the substrate;
etching the gas-sensitive material thin film layer to form a plurality of grooves arranged at intervals, the grooves penetrating the gas-sensitive material thin film layer; and
depositing a metal electrode material into the plurality of grooves by a magnetron sputtering process, so as to form a gas-sensitive material pattern and a metal electrode pattern distributed alternatingly.

14. The method according to claim 9, further comprising:
after forming a gas-sensitive material pattern and a metal electrode pattern in a same layer on a side of the substrate, forming an insulating layer on the metal electrode pattern, the insulating layer being patterned to correspond to the metal electrode pattern.

15. The method according to claim 9, further comprising:
forming an encapsulation layer on a side of the two-dimensional material filter layer facing away from the metal electrode pattern, the encapsulation layer being patterned to correspond to the metal electrode pattern.

16. The method according to claim 15, wherein the step of forming an encapsulation layer comprises:
forming a thin film encapsulation layer on a side of the two-dimensional material filter layer facing away from the metal electrode pattern by a thermal evaporation process; and
etching the thin film encapsulation layer with a fine metal mask to form a patterned encapsulation layer.

\* \* \* \* \*